United States Patent [19]

Barber et al.

[11] Patent Number: 4,542,657

[45] Date of Patent: Sep. 24, 1985

[54] TIME DOMAIN TECHNIQUE TO DETERMINE MEAN FREQUENCY

[75] Inventors: William D. Barber, Ballston Lake; Jeffrey W. Eberhard, Schenectady; Steven G. Karr, Clifton Park, all of N.Y.

[73] Assignee: General Electric Company, Schenectady, N.Y.

[21] Appl. No.: 526,856

[22] Filed: Aug. 26, 1983

[51] Int. Cl.$^4$ ............................................. G01F 1/66
[52] U.S. Cl. ................................. 73/861.25; 128/663; 324/79 R; 324/77 H
[58] Field of Search ............................. 73/861.25, 602; 128/663; 324/77 R, 79 R, 77 B, 77 H; 343/5 NQ, 5 TM, 8; 364/485, 486, 517, 728; 367/90

[56] References Cited

U.S. PATENT DOCUMENTS 4,217,909 8/1980 Papadofrangakis et al. ....... 128/663

OTHER PUBLICATIONS

K. S. Miller et al., "A Covariance Approach to Spectral Moment Estimation", IEEE Trans. on Inf. Theory, vol. IT-18, No. 5, Sep. 1972, pp. 588–596.
L. Gerzberg and J. D. Meindl, "Power-Spectrum Centroid Detector for Doppler Systems Applications", Ultrasonic Imaging 2, 232–261, (Jul. 1980).
B. Angelsen, "Instantaneous Frequency, Mean Frequency, and Variance of Mean Frequency Estimators for Ultrasonic Blood Velocity Doppler Signals", IEEE Trans. on Biomed. Engr., BME-28, pp. 733–741, Nov. 1981.

Primary Examiner—Charles A. Ruehl
Attorney, Agent, or Firm—Donald R. Campbell; James C. Davis, Jr.; Paul R. Webb, II

[57] ABSTRACT

Accurate estimates of the instantaneous mean frequency of a time varying signal are achieved at favorable and adverse signal-to-noise ratios by an improved time domain approach. Demodulated in-phase and quadrature signals are sampled and delayed. Noise in both terms of a simple arc tangent algorithm, whose denominator has products of time samples shifted at least one time period with respect to itself, is uncorrelated and removed by low pass filtering. One embodiment is a pulsed ultrasonic Doppler system with quadrature detection to measure and display blood velocity as a function of time.

13 Claims, 9 Drawing Figures

TIME DOMAIN TECHNIQUE TO DETERMINE MEAN FREQUENCY

BACKGROUND OF THE INVENTION

This invention relates to a method and system to estimate the mean frequency of a signal which has good performance over a wide range of signal-to-noise ratios and is achieved in real time.

An accurate determination of the mean frequency of a time varying signal is desired, for instance, in Doppler ultrasonic velocity measurements where the mean frequency of the signal corresponds to the mean velocity of the sampled flow field. Other applications include frequency and phase modulated communications systems and speech recognition. Acoustic measurements of blood velocity are based on the Doppler effect. Perhaps the major difficulty in these measurements is the accurate determination of the Doppler frequency shift in a noisy environment. A new time domain technique is given for determining the Doppler frequency shift which satisfies this rigid requirement.

Figure 1:
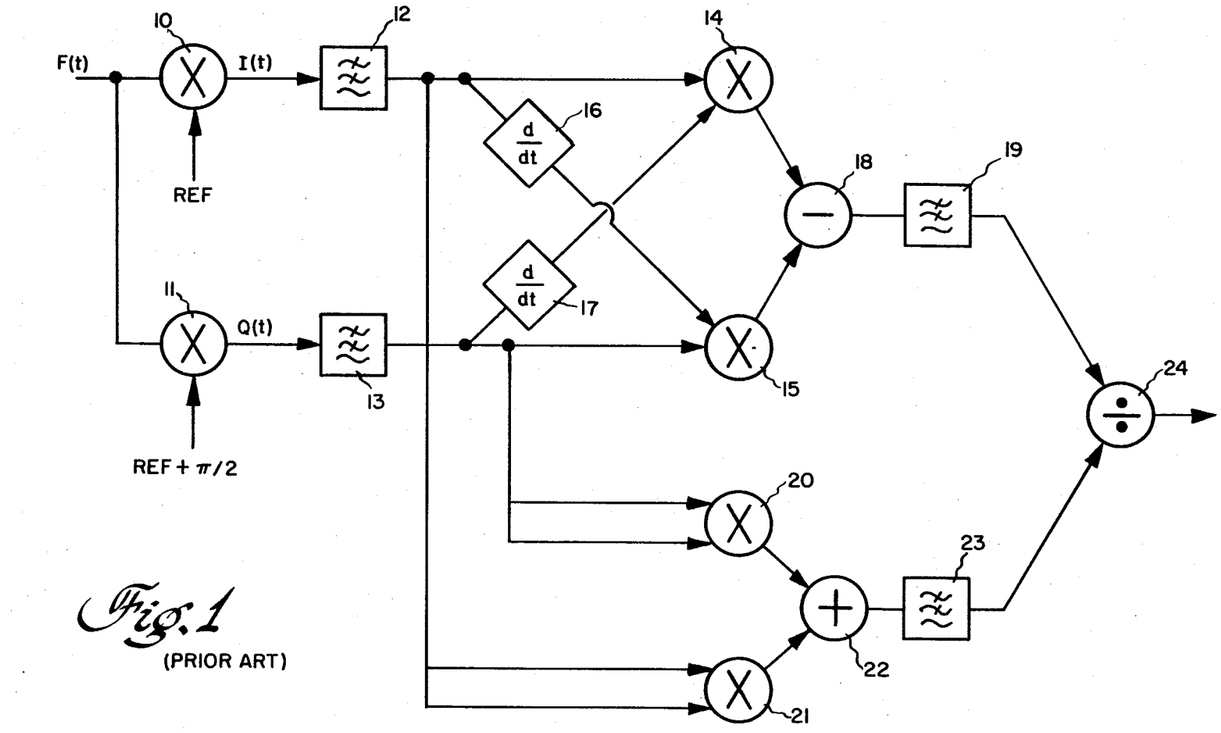
FIG. 1 is a prior art block diagram of signal processing for spectral mean determinations using the I/Q algorithm.

FIG. 1 concerns a prior art implementation of time domain processing using the I/Q algorithm, so named because it derives mean frequency directly from the Doppler I (in-phase) and Q (quadrature) signals. Refer to L. Gerzberg and J. D. Meindl, "Power-Spectrum Centroid Detector for Doppler Systems Applications", Ultrasonic Imaging, Vol. 2, pp. 232-261 (July 1980). It yields results comparable to the Fourier transform technique for high S/N ratio and low frequencies, but it suffers from two major faults. The mean frequency obtained varies as the sine of the true mean frequency and there are false readings for large frequency deviations. When noise is present in the signal, the noise power appears directly in the denominator (in equation (7), $P = I^2 + Q^2$) while the noise is smoothed in the numerator. The noise factor in the denominator leads to gross errors as the S/N ratio approaches unity. The Fourier transform method has a similar form, and the noise power is estimated in order to obtain a reasonable estimate of mean frequency.

SUMMARY OF THE INVENTION

The improved time domain method of determining mean frequency comprises, according to one specific embodiment, demodulating a time varying signal with phase quadrature references, low pass filtering, and simultaneously sampling the demodulated signals. Both the I and Q time samples are delayed by an integer number of time periods, typically one period. The undelayed and delayed time samples are multiplied and a numerator difference signal and denominator sum signal are produced in both of which noise is uncorrelated, the denominator having products of samples shifted one time period with respect to itself. The difference and sum signals are independently low pass filtered and smoothed, such as by a backward running average process, to substantially remove noise in both terms. The mean frequency of the time varying signal is derived from the arc tangent of the ratio of the smoothed difference signal to smoothed sum signal. Improved performance is obtained due to the time shift in the signal correlation functions.

Such a system and process give accurate values for instantaneous frequency, and yield comparable results to the frequency domain Fourier transform approach in good signal-to-noise environments and substantially superior results for signal-to-noise ratios below about 0 dB where the Fourier transform is useless. The mean frequency is linear in the mean power of the spectrum. A third feature of the algorithm is to automatically compensate for frequencies above the Nyquist frequency when determining mean frequency.

An improved ultrasonic method of measuring the velocity of blood and similar liquids, and a pulsed Doppler system, are described and other applications were given. Received echo signals are suitably coherently demodulated to baseband and the focused in-phase and quadrature Doppler signals are range gated at the transmitted pulse repetition frequency. The mean frequency of the Doppler signals corresponds to the frequency shift; mean blood velocity is determined and displayed as a function of time.

DETAILED DESCRIPTION OF THE INVENTION

The fundamental Doppler equation expresses the frequency shift ($\Delta f$) of acoustic energy scattered from a target moving at some velocity (v) in terms of the frequency of the incident wave ($f_o$), the speed of sound in the propagation medium (c), and the angle ($\theta$) between the direction of motion and direction of sound propagation as $$\Delta f = 2f_o(v/c) \cos \theta \quad (1)$$

Rearranging yields a Doppler velocity of $$v = (c/2 \cos \theta)(\Delta f/f_o) \quad (2)$$

In typical applications, c is known, $f_o$ is chosen for convenience, and $\theta$ can be determined. Therefore, determination of $\Delta f$ is tantamount to knowing the scatterer velocity. Numerous techniques exist for deriving particle velocity information from this expression. In this work a phase-coherent pulsed Doppler system was implemented. (See FIG. 5 for a similar system which is part of a duplex imaging system having a common transducer for the imaging and Doppler modalities.) The measured waveform consists of I and Q Doppler signals sampled simultaneously at the Pulse Repetition Frequency, $f_r$(PRF), at a fixed range determined by the delay of the sample pulse with respect to the time of transmission. The goal of the Doppler signal processing is to extract particle or red blood cell velocity information from these measured signals.

Since measured velocities are related to frequency shifts, signal processing in the frequency domain is natural. However, direct time domain methods have certain advantages. Sampled Doppler I and Q signals can be considered as the real and imaginary parts of a complex time domain waveform. The instantaneous frequency of this waveform corresponds to the Doppler shift $\Delta f$ in equation (1). Since the time domain waveform is sampled at the PRF, the Nyquist criterion that two samples per cycle is the minimum to characterize a band-limited signal limits the maximum resolvable frequency to $f_r/2$. However, since both I and Q signals are available, the sign of the shift is known and therefore the direction of scatterer velocity is determined by equation (2).

Representation of a time domain signal by two time domain signals in phase quadrature is common in communication systems where the two signals are derived during the demodulation processes.

$$f(t) = I(t) + iQ(t) \tag{3}$$

The following derivation of an algorithm to determine mean frequency is applicable to frequency and phase modulation communications systems, speech recognition, Doppler ultrasonic velocity measurements, and possibly other applications. The mean frequency, $\omega$, of this signal can be determined from the power spectrum, $S(\omega)$, of the signal by the relation $$\bar{\omega} = \frac{\int_{-\infty}^{\infty} \omega S(\omega) \, d\omega}{\int_{-\infty}^{\infty} S(\omega) \, d\omega} \tag{4}$$

The power spectrum is generally found by taking the Fourier transform of the signal, f, and squaring the amplitude of the transform (the asterisk designates the complex conjugate form):

$$S(\omega) = \hat{f}^* \hat{f} \tag{5}$$

It can be shown, by using Plancherel's theorem and Fourier transform identities, that the mean frequency may also be expressed as time integrals instead of integrals over frequency. The equivalent time integral form is:

$$\bar{\omega} = \frac{\frac{i}{2} \int_{-\infty}^{\infty} \left[ f(t) \frac{df^*}{dt} - f^*(t) \frac{df}{dt} \right] dt}{\int_{-\infty}^{\infty} f^*(t) f(t) \, dt} \tag{6}$$

If one expresses the signal in terms of the I and Q form of equation (3) then the mean frequency of the expression becomes:

$$\bar{\omega} = \frac{\int_{-\infty}^{\infty} \left( I \frac{dQ}{dt} - Q \frac{dI}{dt} \right) dt}{\int_{-\infty}^{\infty} (I^2 + Q^2) \, dt} \tag{7}$$

This is the I/Q algorithm previously referred to. In a pulsed Doppler system the time signal is not continuous but is a discrete sampled data signal. Attempts to determine mean frequency from a difference equation representation of equation (7) have not been successful. In the denominator there is a power term, so noise is correlated and results in large errors as the S/N ratio approaches unity, and other faults were identified.

A hardware representation of a prior art system to implement the spectral mean directly by using this technique is shown in FIG. 1. The continuous frequency-modulated time varying signal F(t) is presented to two product demodulators 10, 11 which have references shifted 90° with respect to each other, to remove the carrier. Demodulated signals I(t) and Q(t) are passed through low pass filters 12, 13 (the legend shows that the center and high frequencies are blocked) to recover the envelope and fed to multipliers 14, 15. The derivatives are taken at 16, 17 and sent to the multipliers whose outputs are the cross terms shown in the numerator. The cross terms are subtracted at 18 and the result presented to low pass filter 19 to perform the integration. The demodulated in-phase and quadrature signals are squared in multipliers 20, 21 and the sum of the squares taken at 22 as shown in the denominator, and integrated by low pass filter 23. The ratio derived by divider 24 is the mean frequency $\omega$.

If instead we use the complex form of representation:

$$f(t) = A(t) \exp(i\theta(t)) \tag{8}$$

Then equation (7) becomes $$\bar{\omega} = \frac{\int_{-\infty}^{\infty} A^2 \frac{d\theta}{dt} \, dt}{\int_{-\infty}^{\infty} A^2 \, dt} \tag{9}$$

The instantaneous phase in terms of I and Q is $$\theta(t) = \tan^{-1}(Q/I) \tag{10}$$

The derivative of phase, $d\theta/dt$, gives the instantaneous frequency, $\omega$. If one differentiates equation (10) and uses the identity $$A^2 = I^2 + Q^2 = P(t) = P \tag{11}$$

where P(t) is the instantaneous power, then it is easy to show that equations (7) and (9) are identical.

By this invention equations (9) and (10) are implemented in a way which produces superior determination of the mean frequency of a signal. The implementation is based on the recognition of a mathematical subtlety which has been overlooked until now. Using these equations as the starting point, then the mean frequency of the sampled signal is $$\omega_i = \frac{\frac{1}{\Delta t} \sum_{k=i-N}^{i} P_k \Delta\theta_k}{\sum_{k=i-N}^{i} P_k} \tag{12}$$

where $\Delta t$ is the time between samples (assumed uniform), i is the sample number, and N+1 is the total number of samples, and where $$\theta_i = \tan^{-1}(Q_i/I_i) \tag{13}$$

and $$\Delta\theta_i = \theta_i - \theta_{i-1} \quad (14)$$

The superior performance is achieved by recognizing that $\Delta\theta_i$ can be expanded in analytic form rather than simply taking the difference in two computed phases. The difference then becomes $$\Delta\theta_i = \tan^{-1}\left(\frac{Q_i}{I_i}\right) - \tan^{-1}\left(\frac{Q_{i-1}}{I_{i-1}}\right) \quad (15)$$

or $$\Delta\theta_i = \tan^{-1}\frac{I_iQ_{i-1} - Q_iI_{i-1}}{I_iI_{i-1} + Q_iQ_{i-1}} \quad (16)$$

The numerator term in this last expression is the same as if equation (7) were implemented using finite difference techniques, assuming samples at equal finite time intervals, but the denominator is significantly different. It consists of the products of time samples shifted one time period with respect to itself. It is the first delayed term of the autocorrelation function and is not the power. The result is that noise, in both terms (the numerator has cross terms), can be smoothed independently. Provided that the sample delay time is greater than the correlation time of the noise, the noise will be smoothed and therefore reduced with respect to the signal. This condition is easy to achieve in practice.

The preferred implementation of equation (16) uses the fact that the instantaneous power, P(t), is relatively constant over the time for determination of the mean frequency.

This means that the approximation $$\overline{\omega} = \frac{\Delta\theta_i}{\Delta t} \quad (17)$$

is valid and one can use the smoothed form which has smoothing in both the numerator (N) and denominator (D):

$$\overline{\omega} = \frac{1}{\Delta t} \tan^{-1}\left(\frac{N_i}{D_i}\right) \quad (18)$$

where $$N_i = (1-\alpha)N_{i-1} + \alpha(I_iQ_{i-1} - Q_iI_{i-1}) \quad (19)$$

$$D_i = (1-\alpha)D_{i-1} + \alpha(I_iI_{i-1} + Q_iQ_{i-1}) \quad (20)$$

The factor $\alpha$ is less than unity; an optimum value is selected and is application dependent. Typical values for Doppler measurements are 1/16 to 1/256. The running averages in equations (19) and (20) replace the sums found in other equations. Two key features in the signal permit a marked improvement in the S/N ratio. First, the terms $I_iQ_{i-1} - Q_iI_{i-1}$ and $I_iI_{i-1} + Q_iQ_{i-1}$ change slowly with time in most practical applications, the rate of change being much lower than the instantaneous frequency of I or Q alone. Therefore, smoothing does not significantly impact the frequency response of the system. Second, the denominator terms form a cross correlation function at one time delay interval. For uncorrelated noise, the noise term should converge to zero for long smoothing times.

Figure 2:
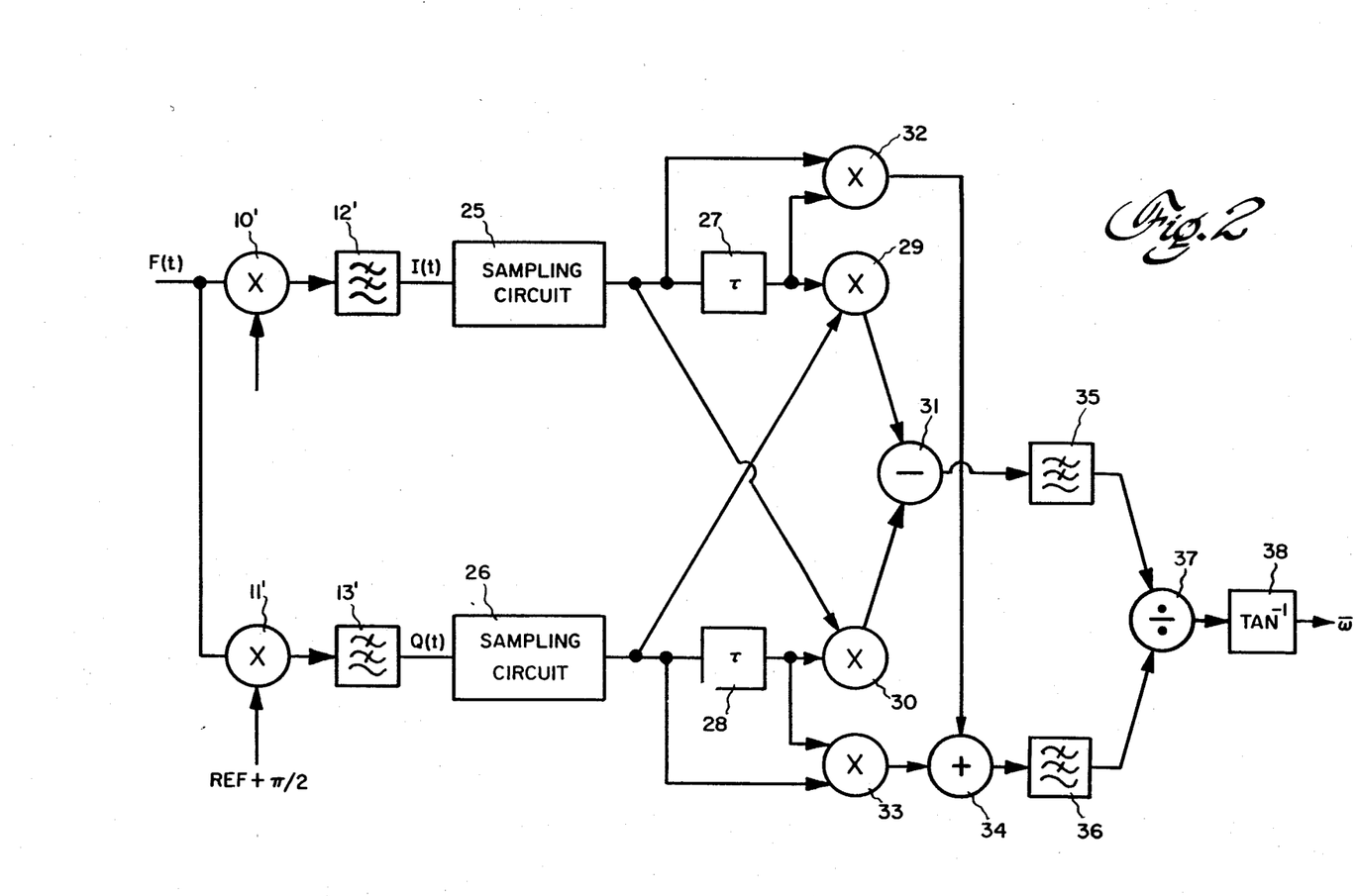
FIG. 2 is a block diagram and hardware representation of a system to implement the improved time domain technique of mean frequency determination using the instantaneous frequency algorithm.
Figure 3A:
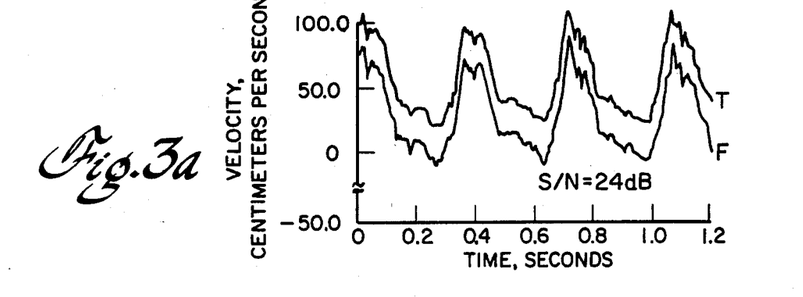
FIGS. 3a-3e show graphically a comparison of pulsatile velocity measurements using time (T) and frequency (F) domain signal processing for various signal-to-noise ratios: (a) S/N=24 dB, (b) S/N=4 dB, (c) S/N=0 dB, (d) S/N=−4 dB, and (e) S/N=−8 dB.
Figure 3B:
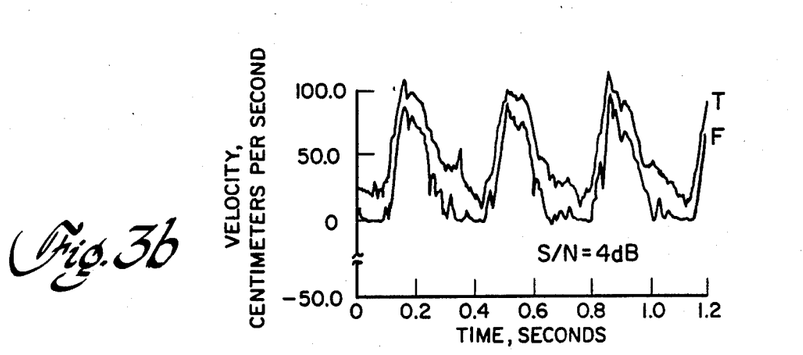
Figure 3C:
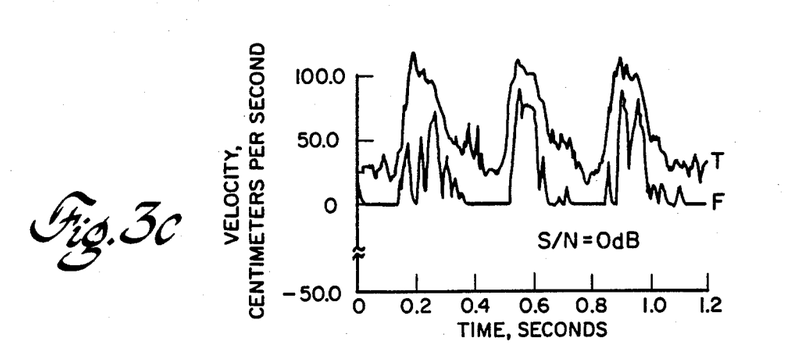
Figure 3D:
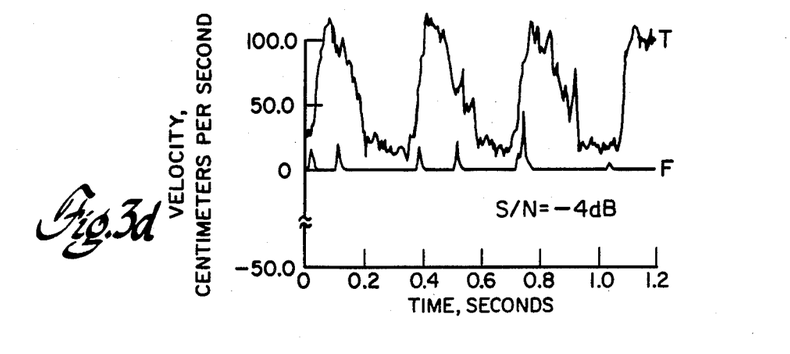
Figure 3E:
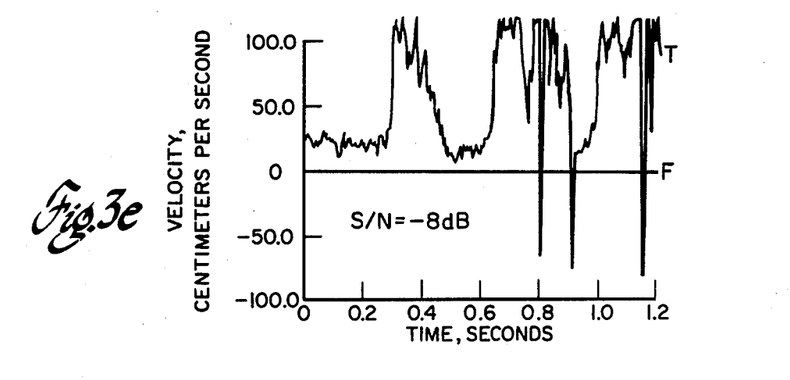

FIG. 2 is a block diagram of signal processing for spectral mean determinations using the instantaneous frequency algorithm, equations (18), (19) and (20). It is for continuous and sampled time domain signals but the latter is illustrated and explained. The demodulators 10' and 11' which have phase quadrature references and low pass filters 12' and 13' to remove residual carrier frequency and other higher harmonics, may be the same as in FIG. 1 and are identified by primed numerals. The initial step in the detection process is generally to demodulate the signal in order to remove the carrier. The optimum performance is achieved by using synchronous detection. The demodulation may be directly to baseband (homodyne) or through intermediate frequencies (heterodyne). The filtered, demodulated in-phase and quadrature signals, I(t) and Q(t), are sampled at a designated rate in sampling circuits 25 and 26 and digitized at this point. The individual functions may be implemented with any current or future technology either digital, analog, or hybrid digital/analog. The key elements are the delay operations, $\tau$, which produce the improved performance due to the time shift in the signal correlation functions. The in-phase and quadrature time samples are delayed an integer number of time periods, preferably one time period, by time delay devices 27 and 28. The delayed in-phase samples and undelayed quadrature samples are presented to a multiplier 29. Correspondingly, the delayed quadrature samples and undelayed in-phase samples are presented to multiplier 30. The first of these cross terms is subtracted from the second at 31 to produce a difference signal in which noise is uncorrelated. The delayed and undelayed in-phase time samples are fed to a third multiplier 32, and the delayed and undelayed quadrature time samples to fourth multiplier 33, and these products are added in summer 34 to produce a sum signal in which noise is uncorrelated. The denominator consists of the products of time samples shifted one time period with respect to itself, hence noise is not correlated.

The numerator difference signal and denominator sum signal are independently and separately low pass filtered to smooth and substantially remove noise from both. Equations (19) and (20) derive the smoothed numerator and denominator terms by a backward running average process. In the first, the old numerator term is multiplied by $(1-\alpha)$ and added to the new numerator which is multiplied by $\alpha$. The factor $\alpha$, typically 1/16 to 1/256, refers to the number of time samples, 16 to 256, that are averaged. The smoothed and substantially noise-free difference and sum signals are divided at 37, and the output signal, the mean frequency of the time varying signal, $\omega$, is produced by determining the arc tangent of this ratio. Getting the arc tangent can be done at a lower rate than sampling.

An example of the performance of the instantaneous frequency algorithm compared to the mean frequency computed by the Fourier transform is shown in FIGS. 3a-3e. The curve labeled F is the result obtained by a Fourier transform with a correction made for the mean noise power. Curve T is the time domain algorithm of equation (18) with $\alpha = 1/64$. Curve T has been offset 25 units for comparison purposes. Each figure is for a different experimental measurement with a different signal-to-noise ratio. These are, respectively, 24 dB, 4 dB, 0 dB, $-4$ dB, and $-8$ dB. At 0 dB the peaks in curve F are still distinguishable, but below this the Fourier transform is useless and in the last line curve F is in fact a straight line. With the improved time domain technique, on the other hand, reasonable performance is achieved for a signal-to-noise ratio of −4 dB, and even at −8 dB significant features of the velocity curve are still recognizable. The ability of the time domain algorithm to extract mean frequency and velocity information in a noisy environment is a major advantage of this technique.

Figure 4:
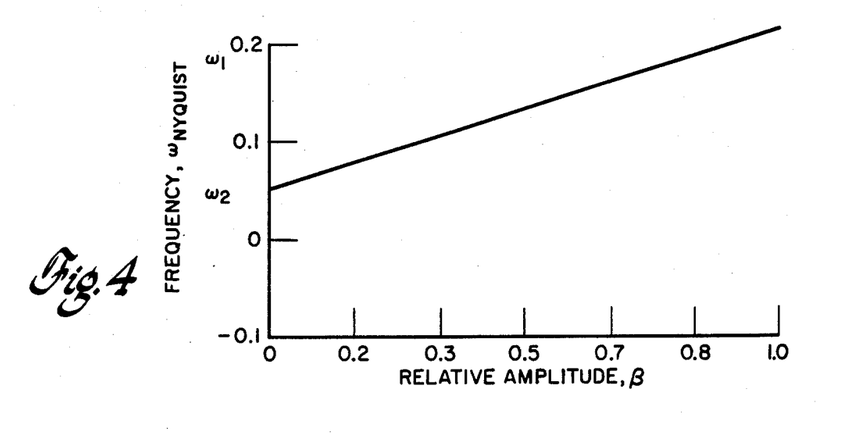
FIG. 4 shows the frequency response to the arc tangent algorithm for two spectral lines with different relative power but constant total power.

A second feature of this algorithm is that the mean frequency computed is linear in the mean power of the spectrum. This is demonstrated in FIG. 4 where two frequencies $\omega_1$ and $\omega_2$ are present and the total power is varied linearly between $\omega_2$ and $\omega_1$ by the ratio $\beta$ where $\beta = P_{\omega 1}/P_{total}$. It is seen that the mean frequency is given by $\omega = \beta\omega_1 + (1-\beta)\omega_2$.

A third, and important, feature of the algorithm is the ability of the algorithm to automatically compensate for frequencies above the Nyquist frequency when computing the mean frequency. This will be true as long as the full spectrum of the instantaneous signal centered at the mean frequency lies in an interval whose width is less than the Nyquist interval. This is useful in determining the mean frequency when aliasing has occurred.

The mean frequency of a frequency-modulated time varying signal is obtained according to the invention either by hardware circuitry, digital, analog, or hybrid digital/analog, or by use of a computer. In a digital hardware system, referring to FIG. 2, the time delay can be determined by one or more clock cycle delays and there are certain advantages in using more than one time delay. In an analog system the delay can be obtained by means of a delay line. In sampled data systems, CCD (Charge Coupled Device) type devices, bucket brigades, and similar devices can be used to obtain the delay as well as performing some of the signal processing. In a system implementation, a special arithmetic processing chip, such as an Intel 8231A, could be used to implement most, if not all, of these functions using sufficient memory. The arc tangent can be implemented by identifying the angular interval within 45° by testing the signs and relative magnitudes of the numerator and denominator terms. Once the argument is known within 45° a piecewise linear approximation can be used.

Figure 5:
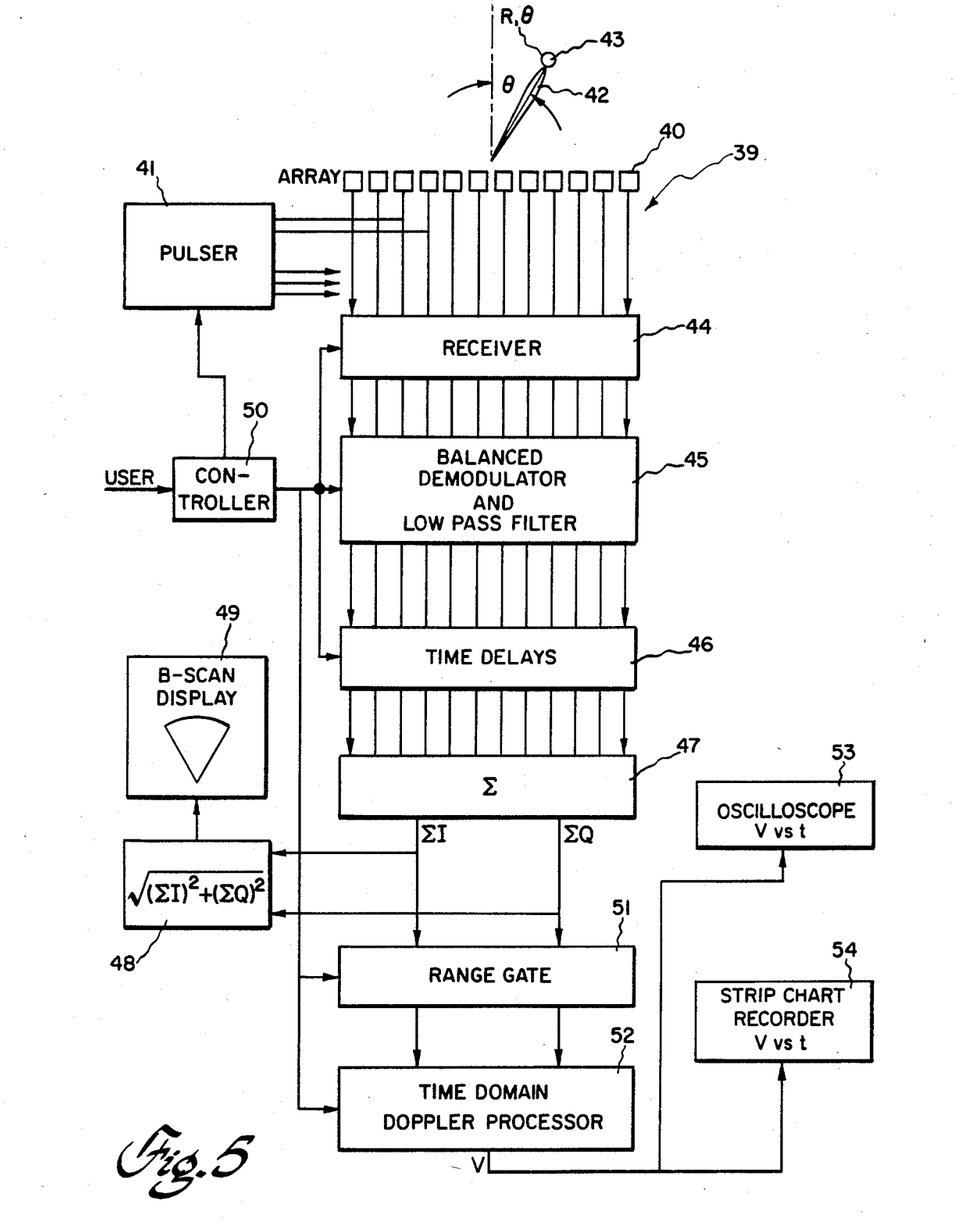
FIG. 5 is a simplified block diagram of a duplex ultrasonic imaging system which incorporates the time domain Doppler processor of the invention.

The duplex imaging system in FIG. 5 is a real time single sector steered beam scanner into which is incorporated an improved time domain Doppler processor for real time blood flow velocity measurement. It is briefly described here and more detail is given in commonly assigned U.S. Pat. No. 4,217,909 to E. Papadofrangakis and W. E. Engeler, and U.S. Pat. No. 4,155,260 to W. E. Engeler and J. J. Tiemann, the disclosures of which are incorporated herein by reference. It is understood, however, that the pulsed Doppler system can be built as a separate unit and need not be part of a duplex system with B-scan imaging capability. The illustrated equipment has a common linear transducer array 39 comprised of a large number of transducer elements 40 which are energized by a pulser 41 to form an ultrasound beam 42 and transmit a pulse of ultrasound. During the Doppler mode of operation the beam is directed at a scan angle $\theta$ and transmitted ultrasound pulses insonify the chosen sample volume 43, which is at range R and through which the velocity of blood flow is being measured. The major components of the receiving channels, which feature baseband signal processing to achieve good lateral resolution while greatly reducing the required time delay accuracy and instead requiring more easily achievable phase focusing accuracy, are a broadband receiver 44 for every channel, a balanced demodulator and low pass filter 45, a time delay device 46, and summers 47. The individual receiving channels have parallel I(in-phase) and Q(quadrature) processing channels in which the received echo signals are electronically steered and dynamically focused. Echo signals are amplified and demodulated using phase quadrature emission frequency references, and the output of each demodulator is low pass filtered to preserve the envelope and then delayed. Where path lengths differ sufficiently, a delay proportional to the path length difference is provided before coherent summation. In the imaging mode of operation the summed and focused signals are presented to circuit 48 to yield a resultant which is the video signal fed to cathode ray tube 49 to build up the sector-shaped image.

In the Doppler operating mode, system controller 50 is set by the user such that rf pulses of ultrasound are transmitted to insonify the sample volume 43, and range gating is employed to sample echoes from the desired depth and detect velocity patterns at the specific location. Another feature of the transducer excitation is variable repetition intervals in order to be able to adequately sample, at various ranges, backscattered echoes from slow as well as fast moving blood cells in the sample volume. Several ultrasound pulse repetition frequency (PRF) settings are provided, such as 4 KHz, 8 KHz, and 16 KHz. The summed and focused I and Q signals are fed directly to the Doppler system without generating their resultant. The focused in-phase and quadrature signals $\Sigma I$ and $\Sigma Q$ are sampled at a specific time after each transducer excitation interval which corresponds to the time taken for the ultrasonic signal to return to the transducer from range R. A range gate 51 is opened by controller 50 for a relatively short interval at a time corresponding to reception of echoes backscattered from the sample volume and extracts a pair of analog time samples in parallel. It is seen that the sampling rate is determined by the pulse repetition frequency. The in-phase and quadrature time samples are digitized and presented to the time domain Doppler processor 52 where the mean frequency of the time varying Doppler signal is derived using the arc tangent algorithm. Blood velocity is then obtained from equation (2).

The ultrasonic system has two types of Doppler mode display devices for velocity information. The Doppler frequencies are first displayed on an oscilloscope 53 so that the user can observe their variation in real time. A hard copy of the evolution of velocity versus time is printed up by a strip chart recorder 54. Either an averaged mean velocity or the entire distribution of velocities (positive and negative corresponding to blood flow toward and away from the transducer array) can be displayed. A multiplexed ECG signal provides a time reference for events occurring during the course of a heart cycle.

The time domain Doppler processor 52 is preferably implemented in hardware as are most real time frequency domain Fourier processors. To study such a pulsed Doppler system a software implementation of the algorithm was used to compute the time domain analysis. The program computed the running average of the numerator and denominator of the argument of the arc tangent. After taking the arc tangent of the ratio, the calculated change in phase with time is compared to the cutoff frequency of the high pass filter designed to block dc and low frequency components. If it is in the stop band of the filter, then a simple I/Q approximation was used to estimate the change in phase. Once the change in phase is computed, it is multiplied by the conversion factor to obtain velocity. The present values of I and Q are then stored to form the new delayed value.

The ease of determining the instantaneous mean frequency, using this technique, has led to other related signal processing features to be used in spectral estimation. The first concerns a time-frequency histogram. In many applications one desires an estimation of the actual spectrum. This is commonly done using the Fourier transform. By an extension of the time domain technique, an approximate spectrum distribution can be obtained by forming a histogram of the instantaneous power versus the instantaneous frequency. The second feature concerns correction of I and Q demodulator unbalance. In Doppler and other quadrature phase demodulation systems, the final system accuracy is affected by the accuracy of the I and Q demodulator balance. A new technique was developed which involves multiplexing the detectors.

Other applications of this process of determining the mean frequency of a time varying signal include frequency and phase modulated communications systems and speech recognition. In the first-mentioned, the mean frequency circuitry is utilized as an FM detector. The resulting output recovers the modulated signal on the carrier. For speech recognition, the measured mean frequency is the information (voice) signal impressed on the carrier, and is an indication of the mean pitch of the voice. The voice track is sampled and digitized and the time domain algorithm is used to pick out mean frequencies from which the pitch of the voice is ascertained.

In conclusion, the superior performance of this improved time domain technique and its ease of implementation favors time domain signal processing. Such a system has the advantages of enhanced ability to deal with noisy environments and greater performance at lower cost compared to the classical Fourier transform approach.

While the invention has been particularly shown and described with reference to preferred embodiments thereof, it will be understood by those skilled in the art that various changes in form and details may be made therein without departing from the spirit and scope of the invention.

The invention claimed is:

1. The method of determining the mean frequency of a frequency-modulated time varying signal having a wide range of signal-to-noise ratios by an improved time domain technique comprising:

demodulating said time varying signal with phase quadrature references and sampling the demodulated signals at designated time periods to yield in-phase and quadrature samples;

delaying said in-phase and quadrature samples by an integer number of time periods and multiplying the first with an undelayed quadrature sample and the second with an undelayed in-phase sample, and subtracting the respective cross terms to produce difference signals;

multiplying said delayed and undelayed in-phase time samples, and delayed and undelayed quadrature time samples, and adding these products to produce sum signals in which noise is uncorrelated;

separately low pass filtering said difference and sum signals to smooth and substantially reduce noise in both, and dividing the former by the latter; and deriving the mean frequency of said time varying signal from the arc tangent of the just-mentioned ratio.

2. The method of claim 1 wherein said time samples are all delayed by one time period.

3. The method of claim 1 wherein said difference and sum signals are filtered and smoothed by a backward running average process.

4. An ultrasonic method of measuring the velocity of the flow of blood and similar liquids comprising the steps of:

transmitting pulses of ultrasound to insonify a chosen sample volume and receiving echo signals that are demodulated using phase quadrature emission frequency references and processed to produce focused in-phase and quadrature Doppler signals;

range gating said Doppler signals after every pulse transmission to extract in-phase and quadrature time samples whose period is determined by the pulse repetition frequency;

delaying said in-phase and quadrature samples by at least one time period and multiplying the first with an undelayed quadrature sample and the second with an undelayed in-phase sample and subtracting the respective cross terms to produce difference signal samples;

multiplying said delayed and undelayed in-phase time samples, and delayed and undelayed quadrature time samples, and adding these products to produce sum signal samples in which noise is uncorrelated;

separately low pass filtering said difference and sum signals to smooth and substantially reduce noise in both;

deriving the mean frequency of said Doppler signals and thus the frequency shift from the arc tangent of the ratio of said smoothed difference signal to smoothed sum signal; and determining mean blood velocity from said mean frequency and displaying velocity as a function of time.

5. The method of claim 4 wherein said difference and sum signals are filtered and smoothed by a backward running average process.

6. The method of claim 5 wherein Doppler frequency shift and blood velocity are determined in real time.

7. An ultrasonic system for measuring the velocity of blood and similar liquids comprising:

means for transmitting pulses of ultrasound that insonify a chosen sample volume and for receiving echoes;

means for coherently demodulating echo signals to baseband using phase quadrature emission frequency references and focusing and summing to produce in-phase and quadrature time varying Doppler signals;

means for simultaneously gating said Doppler signals after pulse transmissions to extract in-phase and quadrature time samples, $I_i$ and $Q_i$, representing echoes backscattered from the sample volume;

means for determining the mean frequency, $\bar{\omega}$, of said time varying signal in real time at favorable and adverse signal-to-noise ratios, and thus the frequency shift, by producing delayed time samples $I_{i-1}$ and $Q_{i-1}$ and processing said undelayed samples $I_i$ and $Q_i$ and delayed samples so as to smooth and remove substantially all uncorrelated noise; and means for deriving mean blood velocity from said mean frequency and displaying velocity as a function of time.

8. The system of claim 7 wherein said mean frequency determining means implements the time domain algorithm $$\bar{\omega} = \frac{1}{\Delta t} \tan^{-1}\left(\frac{N_i}{D_i}\right)$$

where $$N_i = (1-\alpha)N_{i-1} + \alpha(I_i Q_{i-1} - Q_i I_{i-1})$$

$$D_i = (1-\alpha)D_{i-1} + \alpha(I_i I_{i-1} + Q_i Q_{i-1}),$$

where $\Delta t$ is the interval between samples, i=time sample number, N=numerator, D=denominator, and $\alpha$ is less than unity.

9. The method of claim 8 wherein said gating means extracts time samples at the pulse repetition frequency, and said mean frequency determining means delays said samples by one interval between samples.

10. The method of determining mean frequency at signal-to-noise ratios above and below 0 dB by an improved time domain technique comprising the steps of:
demodulating and filtering a time varying signal to yield demodulated in-phase and quadradure signals;
simultaneously delaying both of the latter by the same amount;
multiplying undelayed in-phase and delayed quadrature signals, and undelayed quadrature and delayed in-phase signals, and subtracting the respective cross terms to yield a difference signal;
multiplying undelayed and delayed in-phase signals, and undelayed and delayed quadrature signals, and adding the products to form a sum signal in which noise is uncorrelated;
separately low pass filtering said difference and sum signals to smooth and substantially remove noise in both; and
deriving an output signal representative of the mean frequency of said time varying signal by determining the arc tangent of the ratio of said smoothed difference and sum signals.

11. The method of claim 10 wherein said demodulated signals are produced by homodyne demodulation to baseband and low pass filtering to remove residual carrier frequency and other harmonics.

12. A system for estimating mean frequency by an improved time domain technique comprising:
means for demodulating and low pass filtering a time varying signal to yield demodulated in-phase and quadrature signals;
means for simultaneously sampling said demodulated signals at designated time periods to extract in-phase and quadrature time samples; and
means for determining the mean frequency of said time varying signal at signal-to-noise ratios above and below 0 dB, including:
means for delaying said time samples by an integer number of time periods;
means for multiplying undelayed in-phase and delayed quadrature samples, and undelayed quadrature and delayed in-phase samples, and producing a difference signal;
means for multiplying undelayed and delayed in-phase samples, and undelayed and delayed quadrature samples, and producing a sum signal in which noise is uncorrelated;
means for separately smoothing said difference and sum signals to substantially remove uncorrelated noise; and
means for deriving the arc tangent of the ratio of said smoothed difference signal to smoothed sum signal.

13. The system of claim 12 wherein said delaying means simultaneously delays said time samples by one time period, and said smoothing means is comprised of moving average filters.

* * * * *